(12) United States Patent
Tranchant et al.

(10) Patent No.: US 11,319,390 B2
(45) Date of Patent: *May 3, 2022

(54) POLY(ETHYLENE GLYCOL) METHACRYLATE MICROGELS, PREPARATION METHOD AND USES

(71) Applicants: LVMH RECHERCHE, Saint-Jean de Braye (FR); CENTRE NATIONAL DE LA RECHERCHE SCIENTIFIQUE, Paris (FR); UNIVERSITE DE PAU ET DES PAYS DE L'ADOUR, Pau (FR)

(72) Inventors: Jean-Francois Tranchant, Marigny les Usages (FR); Emilie Gombart, Orleans (FR); Laurent Billon, Saint Faust (FR); Maud Save, Escala (FR); Mohamed Boularas, Pau (FR)

(73) Assignees: LVMH RECHERCHE, Saint-Jean de Braye (FR); CENTRE NATIONAL DE LA RECHERCHE SCIENTIFIQUE, Paris (FR); UNIVERSITE DE PAU ET DES PAYS DE l'ADOUR, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/927,616

(22) Filed: Jul. 13, 2020

(65) Prior Publication Data
US 2020/0377674 A1 Dec. 3, 2020

Related U.S. Application Data

(63) Continuation of application No. 16/359,657, filed on Mar. 20, 2019, now Pat. No. 10,745,527, which is a continuation of application No. 15/541,999, filed as application No. PCT/FR2015/050019 on Jan. 6, 2015, now Pat. No. 10,287,403.

(51) Int. Cl.
| | |
|---|---|
| *C08F 220/28* | (2006.01) |
| *B01J 13/00* | (2006.01) |
| *A61Q 19/00* | (2006.01) |
| *A61Q 1/00* | (2006.01) |
| *A61K 8/02* | (2006.01) |
| *A61K 8/04* | (2006.01) |
| *A61K 8/81* | (2006.01) |
| *C08G 65/34* | (2006.01) |
| *C08G 81/02* | (2006.01) |
| *C08J 3/075* | (2006.01) |

(52) U.S. Cl.
CPC ........ *C08F 220/282* (2020.02); *A61K 8/0216* (2013.01); *A61K 8/042* (2013.01); *A61K 8/8152* (2013.01); *A61Q 1/00* (2013.01); *A61Q 19/00* (2013.01); *B01J 13/0052* (2013.01); *C08G 65/34* (2013.01); *C08G 81/025* (2013.01); *C08J 3/075* (2013.01); *A61K 2800/412* (2013.01); *A61K 2800/47* (2013.01); *A61K 2800/882* (2013.01); *A61K 2800/95* (2013.01); *C08F 220/281* (2020.02); *C08G 2115/00* (2021.01); *C08G 2261/128* (2013.01); *C08G 2261/1426* (2013.01)

(58) Field of Classification Search
CPC ....... C08J 3/075; C08J 13/0052; A61K 8/042; A61K 8/8152; C08F 220/18; C08G 65/34; C08G 81/025; C08G 2261/128; C08G 2261/1426
USPC ........................................................... 524/5
See application file for complete search history.

(56) References Cited

U.S. PATENT DOCUMENTS

| | | | |
|---|---|---|---|
| 7,914,710 B2 | 3/2011 | Winnik et al. | |
| 8,158,005 B1 | 4/2012 | Gupta et al. | |
| 10,287,403 B2 * | 5/2019 | Tranchant | C08F 220/28 |
| 10,745,527 B2 * | 8/2020 | Tranchant | B01J 13/0052 |
| 2010/0076105 A1 * | 3/2010 | Hu | C08L 33/26 |
| | | | 522/33 |
| 2012/0028834 A1 | 2/2012 | Kwon et al. | |

FOREIGN PATENT DOCUMENTS

| | | |
|---|---|---|
| WO | 9745202 | 12/1997 |
| WO | 2004081072 | 9/2004 |
| WO | 2006037901 | 4/2006 |
| WO | 2006037907 | 4/2006 |

OTHER PUBLICATIONS

International Search Report issued in International Application No. PCT/FR2015/050019 dated Sep. 21, 2015 (9 pages).
Written Opinion issued in International Application No. PCT/FR2015/050019 dated Sep. 21, 2015 (5 pages).
Boularas et al.: "Design of Smart Oligo (ethylene glycol)-Based Biocompatible Hybrid Microgels loaded with Magnetic Nanoparticles"; Macromolecular Rapid Communications, 2014, vol. 36, pp. 79-84.
Chi et al.: "Oligo(ethylene glycol)-Based Thermoresponsive Core-Shell Microgels"; Langmuir, 2009, vol. 25, pp. 3814-3819.
Zhou et al.: "Engineering oligo(ethylene glycol)-based thermosensitive microgels for drug delivery applications"; Polymer, 2010, vol. 51, pp. 3926-3933.
Wang et al.: "Preparation of biocompatible nanocapsules with temperature-responsive and bioreducible properties"; Journal of Materials Chemistry, 2011, vol. 21, pp. 15950-15956.

(Continued)

*Primary Examiner* — Hui H Chin
(74) *Attorney, Agent, or Firm* — Hamre, Schumann, Mueller & Larson, P.C.

(57) ABSTRACT

The invention relates to poly(oligo(ethylene glycol) methacrylate) microgels, to the process for preparing same and the uses thereof in various fields of application such as optics, electronics, pharmacy and cosmetics.
These microgels have the advantage of being monodisperse, pH-responsive and temperature-responsive. They can carry magnetic nanoparticles or biologically active molecules. These microgels may also form transparent films, which have novel optical and electromechanical properties.

11 Claims, 12 Drawing Sheets

(56) References Cited

OTHER PUBLICATIONS

Nolan et al.: "Thermally Modulated Insulin Release from Microgel Thin Films"; Biomacromolecules, 2004, vol. 5, pp. 1940-1946.
Serpe et al.: "Doxorubicin Uptake and Release from Microgel Thin Films"; Biomacromolecules, 2005, vol. 6, 408-413.
Tian et al.: "Colorful humidity sensitive photonic crystal hydrogel"; Journal of Materials Chemistry, 2008, vol. 18, No. 10, pp. 1053-1160.
Jiang et al.: "Photonic crystal pH and metal cation sensors based on poly(vinyl alcohol) hydrogel"; New Journal of Chemistry, 2012, vol. 36, pp. 1051-1056.
Wu, W. et al., "Multi-functional core-shell hybrid nanogels for pH-dependent magnetic manipulation, fluorescent pH-sensing, and drug delivery," Biomaterials 32 (2011) 9876-9887, XP028316441.

\* cited by examiner

Table 1. Monomer composition of the microgels

| Microgel | P(MEO$_2$MA-co-OEGMA-co-MAA) microgels | | P(MEO$_2$MA-co-OEGMA-co-MAA)/γ-Fe$_2$O$_3$ hybrid microgels | | |
|---|---|---|---|---|---|
| | 1 | 2 | 3 | 4 | 5 |
| MEO$_2$MA (mmol/L) | 88.4 | 83.9 | 83.9 | 83.9 | 83.9 |
| OEGMA (mmol/L) | 9.82 | 9.36 | 9.36 | 9.36 | 9.36 |
| MAA (mmol/L) | 0 [a] | 4.99 [b] | 4.99 [b] | 4.99 [b] | 4.99 [b] |
| OEGDA (mmol/L) | 1.92 | 1.92 | 1.92 | 1.92 | 1.92 |
| KPS (mmol/L) | 0.86 | 0.86 | 0.86 | 0.86 | 0.86 |
| γ-Fe$_2$O$_3$ (wt%) | 0 | 0 | 4.7 [c] | 9.1 [c] | 16 [c] |
| Morphology of the microgels | | | | | |

[a] Microgel 1 contains 0 mol% of MAA units;
[b] Microgels 2, 3, 4 and 5 contain 3.5 mol% of MAA units incorporated in the microgel (i.e. 70% of initial MAA monomer); [c] Content of γ-Fe$_2$O$_3$ nanoparticles per hybrid microgels determined by thermogravimetric analysis (TGA).

FIG. 14

POLY(ETHYLENE GLYCOL) METHACRYLATE MICROGELS, PREPARATION METHOD AND USES

This application is a continuation application of U.S. application Ser. No. 16/359,657 filed on Mar. 20, 2019, which is a continuation application of U.S. application Ser. No. 15/541,999 filed on Jul. 6, 2017, now issued as U.S. Pat. No. 10,287,403, which is a national stage application under 35 USC 371 of PCT Application No. PCT/FR2015/050019 having an international filing date of Jan. 6, 2015, the entire disclosures of each are hereby incorporated by reference in their entirety.

The invention relates to poly(oligo-(ethylene glycol) methacrylate) microgels, to the process for preparing same in an aqueous medium and to the uses thereof in various fields of application such as optics, electronics, sensors, cosmetics, pharmacy and medical diagnosis.

These microgels have the advantage of being monodisperse, pH-responsive and temperature-responsive and of being able to incorporate organic molecules or inorganic particles. Films prepared from colloidal solutions of these microgels optionally filled with inorganic nanoparticles have very advantageous optical and electromechanical properties.

PRIOR ART

There are several chemistries of temperature-responsive microgels. The main ones are based on poly(N-isopropylacrylamide) (PNIPAM), and less commonly on poly(N-vinylcaprolactam) (PVCL) or on poly(oligo(ethylene glycol) methacrylate).

The various pathways for synthesizing poly(oligo(ethylene glycol) methacrylate) microgels which have been described in the literature involve combinations of monomers such as the di(ethylene glycol) methyl ether methacrylate monomer (M(EO)$_2$MA, somewhat hydrophobic), and the penta(ethylene glycol) methyl ether methacrylate monomer (M(EO)$_5$MA somewhat hydrophilic).

The synthesis of a temperature-responsive and pH-responsive microgel, consisting of a temperature-responsive core based on P(M(EO)$_2$MA-co-M(EO)$_5$MA) and of a shell based on a mixture of poly(oligo(ethylene glycol) methacrylate) and poly(acrylic acid) (P(M(EO)$_2$MA-co-M(EO)$_5$MA-co-AA)) has been described by Chi, C., T. Cai, and Z. Hu, *Oligo(ethylene glycol)-Based Thermoresponsive Core-Shell Microgels*. Langmuir, 2009. 25: p. 3814-3819. These microgels have a core/shell structure with a hydrophobic core and a hydrophilic shell.

It has been suggested to incorporate biologically active molecules into microgels based on poly(oligo(ethylene glycol) methacrylate).

For example, a temperature-responsive microgel consisting of a poly(M(EO)$_2$MA) core and of a P(M(EO)$_2$MA-co-M(EO)$_5$MA) shell and of poly(M(EO)$_2$MA-co-OEGMA) nanocapsules obtained by grafting the polymer onto a sacrificial silica particle have been proposed for the delivery of an active principle respectively by Zhou, et al., *Engineering oligo(ethylene glycol)-based thermosensitive microgels for drug delivery applications*. Polymer, 2010. 51: p. 3926-3933; and by Wang, et al., *Preparation of biocompatible nanocapsules with temperature-responsive and bioreducible properties*, Journal of Materials Chemistry, 2011. 21: p. 15950.

Known hybrid (or nanocomposite) temperature-responsive microgels containing inorganic nanoparticles are microgels based on poly(N-isopropylacrylamide) (PNIPAM). These microgels have the drawback of not being biocompatibie.

A first approach for preparing these materials consists in synthesizing the microgels in the presence of the nanoparticles. This strategy makes the manufacture of these hybrid microgels difficult due to the complexity of the polymerization. The proportion of nanoparticles incorporated is generally small and the microgels are polydisperse. Furthermore, it generally results in a core-shell type architecture within which the nanoparticles are uniformly distributed.

A second approach consists in synthesizing, firstly, the temperature-responsive microgels functionalized by ionic groups. Next, the inorganic nanoparticles are incorporated by coprecipitation of the precursor salts of the nanoparticles. Application WO 2004/081072 describes for example PNIPAM microgels having sodium acrylate (—COO$^-$ Na$^+$) anionic units and the in situ coprecipitation of precursor salts of various nanoparticles such as magnetic (Fe$_3$O$_4$) particles, gold (Au) particles, and quantum dot (CdTe, CdS) particles.

A third approach consists in incorporating the inorganic nanoparticles by solvent transfer. Hydrophobic inorganic nanoparticles are synthesized and dispersed in an organic phase. The temperature-responsive microgels are added to the solution containing the nanoparticles then everything is transferred into aqueous solution, which encapsulates the nanoparticles in the microgels. This method has been the subject of a patent using poly(N-isopropylacrylamide) microgels and Quantum dot (CdS) nanoparticles for applications in photoluminescence (U.S. Pat. No. 7,914,710).

A fourth and final approach consists in synthesizing microgels bearing ionic charges and in adsorbing nanoparticles of opposite charges at the surface of the microgel. The preparation of poly(styrene-co-N-isopropylacrylamide) latex having 2-aminoethyl methacrylate (AEMA) cationic groups has been described in application WO 1997/045202. Magnetic γ-Fe$_2$O$_3$ nanoparticles negatively charged at the surface were adsorbed at the surface of the lattices by electrostatic interaction. The nanoparticles were then trapped in the structure by synthesis of a new outer shell of PNIPAM at the surface of the hybrid lattices.

More recently, nanoparticles bearing a positive charge (TiO$_2$) have been incorporated into a PNIPAM microgel structure charged by units comprising an acrylate (COO$^-$) group (U.S. Pat. No. 8,158,005).

The use of microgels, especially temperature-responsive microgels that have magnetic properties, requires in certain fields their preparation in the form of thin films.

The formation of thin films composed of microgels predispersed in an aqueous phase is a difficult synthesis process since it necessitates reconciling two conflicting factors. Microgels dispersed in an aqueous phase are stabilized by repulsive charges that prevent the microgels from aggregating or settling. However, the microgels must interact with one another to form layers of microgels in order to form a film. Several processes have had to be developed in order to form them.

A first process for self-assembling microgels on a modified surface consists in anchoring microgels to the surface of a substrate pretreated in order to create ionic charges on its surface. The microgels have ionic groups generally derived from the polymerization initiator or from an ionic comonomer. The microgels may be anchored to the surface of a substrate by electrostatic interaction with oppositely charged groups. This technique makes it possible to deposit a thin layer of microgel on the substrate (monolayer technique), but it is also possible to multiply these layers by successive surface treatments (Layer-by-Layer technique). Microgels based on poly(N-isopropylacrylamide-co-acrylic acid) or P(NIPAM-co-AA) have been deposited according to this technique on substrates grafted by 3-aminopropyltrimethoxysilane (APTMS) groups. After each layer of microgel, a polymer having positive charges (poly(allylamine hydrochloride) PAH or polyethylene imine) PEI) was added to the modified substrate in order to regenerate the positive charges for a lower pH at the acidity constant of the amines.

The films of microgels deposited on the substrate have been used for the delivery of an active principle such as insulin for the treatment of diabetes (Nolan, C. M., M. J. Serpe, and L. A. Lyon, *Thermally Modulated Insulin Release from Microgel Thin Films*. Biomacromolecules, 2004. 5(5): p. 1940-1946) or doxorubicin for the treatment of cancerous cells (Serpe, M. J., et al., *Doxorubicin Uptake and Release from Microgel Thin Films*. Biomacromolecules, 2005. 6(1): p. 408-413).

This technique has the advantage of controlling the parameters inherent to the production of a thin film of microgels (such as the film thickness and the structuring of the microgels). The drawback of this process lies in its production complexity which requires the use of particular microgels (charged microgels) and pretreated substrates. This prevents any direct use of the microgels on any surface.

A second process for producing a hydrogel film that encapsulates colloidal particles consists in encapsulating the particles in a hydrogel in order to form a flexible and wet film. This process is mainly studied for photonic applications. The idea is to combine the optical properties of assembled particles with the mechanical properties of the hydrogels in the wet state. Some examples are described in the literature and mainly use polystyrene) particles in the form of hard spheres. E. Tian et al. have assembled poly (styrene-co-methyl methacrylate-co-acrylic acid) particles as several structured layers and have encapsulated everything in a polyacrylamide) hydrogel (Tan, E., et al., *Colorful humidity sensitive photonic crystal hydrogel*. Journal of Materials Chemistry, 2008.18: p. 1116-1122). The combination of the two entities has made it possible to develop photonic hydrogels. More recently, H. Jiang et al. also encapsulated polystyrene) particles in a polyvinyl alcohol) or PVA hydrogel (Jiang, H., et al., *Photonic crystal pH and metal cation sensors based on poly (vinyl alcohol) hydrogel*. New Journal of Chemistry, 2012. 36: p. 1051-1056).

More recently, H. Kim et al. assembled magnetic particles of iron oxide ($Fe_3O_4$) coated with silica oxide ($SiO_2$) under the effect of a magnetic field and encapsulated this assembly in a mixture of polyethylene glycol) diacrylate monomer and a photoinitiator. The photopolymerization of the mixture makes it possible to set the particles in a polyethylene glycol acrylate) resin. The magnetic particles set in the bulk have photonic properties that may be defined by the magnetic field applied (US 2012/0028834). This technique has the advantage of producing more flexible microgel films since the latter are supported by a "soft" hydrogel in solution, and not a solid support. However, the production of these films of particles remains complex and various polymerization steps are necessary, which prevents any spontaneous self-assembly during a direct use of the particles.

A third process for forming microgel films consists in adding reactive functions to the surface of the microgels. This functionality is provided by addition of a comonomer during the synthesis of the microgels. These reactive functions may either form covalent bonds with one another, or form covalent bonds by reaction with another entity. It is then possible to form crosslinking points between each microgel, the whole thing giving a film composed of microgels that are chemically bound to one another. This self-assembly process is mainly studied for photonic applications. The self-assembly process depends on the type of functionality added during the synthesis of the microgels. A vast majority of these studies have focused on the assembly of PNIPAM-based microgels.

A first approach consists in adding poly(acrylic acid) (or PAA) within PNIPAM microgels. The self-assembly of the microgels takes place owing to weak interactions between the carboxylic acid functions of the PAA. The sum of the interactions makes it possible to self-assemble the microgels and to gel the medium.

A second approach that consists in creating covalent bonds has also been proposed, either by addition of a crosslinker to the solution of PNIPAM microgels, or by polycondensation of PNIPAM-co-NMA microgels (NMA: N-methylol acrylamide or N-hydroxymethyl acrylamide). The microgels are self-assembled by simple drying of a dispersion of microgels. The formation of the film requires an additional step of thermal post-polymerization of the crosslinker or of thermal and acid-base catalyzed condensation of the NMA.

One study used oligo(ethylene glycol) methacrylate derivative microgels having surface-polymerizable functions. These microgels were crosslinked by UV photopolymerization during their assembly for photonic applications (US 2010/0076105). However, the film formation requires a very long drying time of around several weeks.

The objective of the invention is to propose an oligo (ethylene glycol) methacrylate microgel that has at least one of the following advantages relative to the microgels of the prior art: monodisperse; pH-responsive; biocompatible; capable of forming hybrid (or nanocomposite) microgels by adsorption of oppositely charged nanoparticles; capable of self-assembling in several layers by simple drying process; capable of forming a transparent film; capable of forming a cohesive and elastic film; in the form of a film, capable of generating an electric potential via compression effect; in the form of a film, capable of diffracting light thus generating a color.

It has been discovered within the context of the present invention that certain poly(oligo(ethylene glycol) methacrylates) have a high film-forming potential by evaporation of water at ambient temperature. In particular, the invention proposes for the first time the self-assembly of magnetic hybrid microgels in the form of a thin film having structuring properties.

The microgel films of the invention have the advantage of being completely self-supported. Since the microgels are not encapsulated or supported, during the film formation the interaction between the microgels and the substrate on which they are deposited, for example the skin, is maximal. The films are obtained by simple drying at ambient temperature and no radical initiator is necessary. The microgels of the invention optionally containing nanoparticles are capable of self-assembling in several layers in order to form a transparent film.

It has also been discovered, within the context of the present invention, that the poly(oligo(ethylene glycol) methacrylate) microgels are polyelectrolyte materials capable of generating an electric field by mechanical action.

DESCRIPTION OF THE INVENTION

The invention relates to poly(oligo(ethylene glycol) methacrylate) microgels endowed with colloidal properties and also a responsiveness to variations of temperature and/or pH in water, owing to the presence of optionally salified —COOH groups.

Within the meaning of the invention a "microgel" is understood to be a crosslinked polymer in the form of a spherical particle having a size that varies from 100 nm to 500 nm in the dry state (i.e. containing less than 2% by weight of water), preferably between 350 and 450 nm, more preferably of the order of 400 nm. The microgel of the invention is a microhydrogel in the sense that it is capable of being obtained by a process of aqueous phase copolymerization of several monomers. The microgel of the invention does not have a core/shell structure: the monomers that form it are distributed uniformly throughout the volume of the particle, which gives it particular properties.

The microgels of the invention may have the advantage of simultaneously being monodisperse, temperature-responsive, pH-responsive and biocompatible. The microgels of the invention may simultaneously be temperature-responsive and biocompatible, unlike the temperature-responsive microgels of the prior art which are generally structures based on poly(alkylacrylamide).

The microgels of the invention have the novelty of comprising a mixture of branched ethylene oxide repeat units and units comprising a carboxylic acid (—COOH) or carboxylate (—COO$^-$) group, the content of which it is possible to vary depending on the targeted applications. These groups give the microgels the pH-responsive property.

A first subject of the invention is thus microgels obtainable by aqueous phase precipitation polymerization of the following three monomers:
  di(ethylene glycol) methyl ether methacrylate (M(EO)$_2$MA),
  an oligo(ethylene glycol) methyl ether methacrylate (M(EO)$_n$MA) n ranging from 3 to 12,
  a monomer of formula $CR_1R_2=CR_3R_4$ in which $R_1$, $R_2$, $R_3$ and $R_4$ represent a hydrogen, a halogen or a hydrocarbon group, at least one of the four groups comprising a —COOH or —COO$^-$M$^+$ group, M$^+$ representing a cation,
  in the presence of a crosslinking agent.

In the remainder of the text, the term "—COOH" denotes the —COOH acid form or —COO$^-$M$^+$ salified form, for simplification.

M(EO)$_2$MA represents for example 50 mol % to 90 mol % of the total number of moles of the monomers, M(EO)$_n$MA preferably represents 10 to 50 mol % of the total number of moles of the monomers and the monomer of formula $CR_1R_2=CR_3R_4$ preferably represents 0.1 mol % to 20 mol % of the total number of moles of the monomers, the sum of these three contents being equal to 100%.

The molar ratio between M(EO)$_2$MA and M(EO)$_n$MA is preferably between 1:1 and 20:1, for example between 5:1 and 10:1. Within the meaning of the invention the expression "between" excludes the numerical limits that succeed it. On the other hand, the expression "ranging from . . . to" includes the stated limits.

The oligo(ethylene glycol) methyl ether methacrylate has a formula (M(EO)$_n$MA) where n ranges from 3 to 12. The number n can range from 7 to 9, or from 7 to 8, or from 8 to 10. The number n can also be 9. The molecular weight Mn of the oligo(ethylene glycol) methyl ether methacrylate can be 475 g/mol.

The number of moles of monomer of formula $CR_1R_2=CR_3R_4$ may be between 0 and 20 mol %, for example ranging from 0.1 to 5 mol % of the total number of total moles of the three monomers.

According to one embodiment, M(EO)$_2$MA represents for example 80 to 90 mol % of the total number of moles of the three monomers, M(EO)$_n$MA preferably represents 5 to 15 mol % of the total number of moles of the monomers and methacrylic acid preferably represents 0.1 to 10 mol % of the total number of moles of the monomers, the sum of these three contents being equal to 100%.

The monomer of formula $CR_1R_2=CR_3R_4$ is preferably such that $R_1$ and $R_2$ each represent a hydrogen, $R_3$ represents H or an alkyl group, preferably a C1-C6 alkyl group, optionally substituted with —OH or —COOH, and $R_4$ represents, independently of $R_3$, the —COOH group or an alkyl group, preferably a C1-C6 alkyl group, optionally substituted with —OH or —COOH. The alkyl group may be methyl, ethyl or n-butyl. According to one particular embodiment, $R_1$ and $R_2$ each represent a hydrogen and $R_3$ and $R_4$ independently represent —H, —COOH, or —CH$_2$—COOH.

The monomer of formula $CR_1R_2=CR_3R_4$ may for example be chosen from methyl acrylic, methyl methacrylic, ethyl acrylic, ethyl methacrylic, n-butyl acrylic and n-butyl methacrylic acids.

According to one embodiment, the monomer of formula $CR_1R_2=CR_3R_4$ may be methacrylic acid or itaconic acid. Acrylic acid may be excluded from the definition of the monomer of formula $CR_1R_2=CR_3R_4$ in certain cases.

The crosslinking agent may be selected from the group consisting of oligo(ethylene glycol) diacrylate comprising from 1 to 10 ethylene glycol units, 1,3-butanediol diacrylate, 1,4-butanediol diacrylate, 1,6-hexanediol diacrylate, pentaerythritol diacrylate monostearate, glycerol 1,3-diglycerolate diacrylate, neopentyl glycol diacrylate, polypropylene glycol) diacrylate, 1,6-hexanediol ethoxylate diacrylate, trimethylolpropane benzoate diacrylate, ethylene glycol dimethacrylate, 1,3-butanediol dimethacrylate, 1,4-butanediol dimethacrylate, 1,6-hexanediol dimethacrylate, glycerol dimethacrylate, N,N-divinylbenzene, N,N-methylenebisacrylamide, N,N-(1,2-dihydroxyethylene)bisacrylamide, polyethylene glycol) diacrylamide, allyl disulfide, bis(2-methacryloyl)oxyethyl disulfide and N,N-bis(acryloyl)cystamine.

The crosslinking agent represents for example from 1 to 5 mol % of the total number of moles of the three monomers.

The monomers used are preferably di(ethylene glycol) methyl ether methacrylate (M(EO)$_2$MA, Mn 250 g.mol$^{-1}$), oligo(ethylene glycol) methyl ether methacrylate (Mn 475 g.mol$^{-1}$), methacrylic acid (MAA).

The crosslinking agent is for example oligo(ethylene glycol) diacrylate comprising 4 to 5 ethylene oxide units (OEGDA, Mn 250 g.mol$^{-1}$). The chemical structures of the preferred monomers and crosslinking agent are represented in FIG. 1.

The mean size of a microgel of the invention may vary depending on whether it is dry or in aqueous solution: thus, a microgel in the dry state may reach four times its initial size when it is placed in aqueous solution at 20° C. The mean size of a microgel of the invention in the dry state may range from 100 to 1000 nm. The hydrodynamic radial distribution function of the microgels measured at an angle of 60° and at a temperature of 20° C., is advantageously less than 1.1, which gives the microgels the quality of being monodisperse.

The microgels of the invention may comprise organic or inorganic particles: in this case they are commonly known as hybrid microgels. The particles introduced preferably have a size of between 1 and 150 nm, for example between 5 and 50 nm, and are known as nanoparticles. The nanoparticles may or may not be magnetic.

A second subject of the invention are monodisperse, temperature-responsive and magnetic hybrid microgels based on poly(oligo(ethylene glycol) methacrylate) containing magnetic nanoparticles, and a process for preparing these hybrid microgels.

Certain monodisperse, temperature-responsive and magnetic hybrid microgels based on poly(oligo(ethylene glycol) methacrylate) of the invention are obtained from at least two monomers:
di(ethylene glycol) methyl ether methacrylate ($M(EO)_2MA$), and
an oligo(ethylene glycol) methyl ether methacrylate ($M(EO)_nMA$) n being an integer ranging from 3 to 12,
and optionally in the presence of a third monomer:
a monomer of formula $CR_1R_2=CR_3R_4$ in which $R_1$, $R_2$, $R_3$ and $R_4$ represent a hydrogen, a halogen or a hydrocarbon group, on condition that at least one of the four groups comprises a —COOH or —COO⁻M⁺ group, such that M⁺ represents a cation.

A process for preparing monodisperse, temperature-responsive and magnetic hybrid microgels based on poly(oligo(ethylene glycol) methacrylate) of the invention consists in:
preparing a colloidal dispersion of nanoparticles that are positively charged at their surface and that are placed in aqueous solution,
preparing an aqueous colloidal dispersion of microgels as claimed in one of claims 1 to 4,
mixing the two colloidal dispersions and adjusting the pH above the isoelectric point of the nanoparticles.

According to one embodiment, the nanoparticles are positively charged at their surface when they are placed in aqueous solution to the extent that the hybrid microgels of the invention may be prepared by simple mixing of two colloidal dispersions: a first colloidal dispersion of microgels and a second colloidal dispersion of nanoparticles. The key parameters enabling the success of this process lie, on the one hand, in the addition of carboxyl or carboxylate groups distributed homogeneously within the microgel and, on the other hand, in the positive surface charge of the nanoparticles. Everything makes it possible to encapsulate the nanoparticles within the microgel in a controlled manner, while preserving the colloidal and temperature-responsive properties of the final material. The hybrid architecture of the microgels and also their temperature-sensitive properties are demonstrated in this invention. The incorporation of the nanoparticles within the microgels is firstly demonstrated with a large and quantitative content of encapsulated magnetic nanoparticles (filler contents tested ranging from 0 to 33 wt % of nanoparticles per hybrid microgel). The temperature-responsive properties of the hybrid microgels in aqueous solution are also demonstrated irrespective of the magnetic nanoparticle filler content.

According to one embodiment, the nanoparticles are pigments, dyes or sunscreens commonly used in the optics, cosmetics, agri-food or pharmacy fields.

The particles may comprise at least one metal or one metal oxide. The metal may be gold, silver, tin, titanium, copper or aluminum. The metal oxide may be selected from the group consisting of iron, titanium, zinc, chromium and tin oxides.

The particles comprise for example at least one of the following compounds: $TiO_2$, $Fe_2O_3$, $TiFe_2O_5$, Ti-suboxides, $Fe_3O_4$, $Cr_2O_3$, $ZrO_2$, $ZnO$, $SnO_2$, $Sn(Sb)O_2$.

According to one embodiment, the nanoparticles are magnetic nanoparticles of iron oxide ($Fe_2O_3$, maghemite) having a size between 1 and 150 nm, for example between 6 and 30 nm.

The magnetic nanoparticles may be synthesized by coprecipitation of metal salts ($Fe^{2+}$ and $Fe^{3+}$) in the aqueous phase, then oxidation in order to produce magnetic nanoparticles ($\gamma$-$Fe_2O_3$) stabilized in solution by positive charges. The process for the synthesis of maghemite nanoparticles may be that developed by Massart, R., *Preparation of aqueous magnetic liquids in alkaline and acidic media*. IEEE Trans. Magn., 1981. 17(2): p. 1247-1248.

The preparation of temperature-responsive hybrid microgels based on poly(oligo(ethylene glycol) methacrylate) and nanoparticles may preferably be carried out by a process of mixing the two constituents in the form of colloidal dispersions. The nanoparticles placed in aqueous solution are capable of being positively charged at the surface when they are brought into contact with the microgels. The stability of the hybrid microgels is obtained by an increase in pH above the isoelectric point of the inorganic nanoparticles while preserving the encapsulation of the nanoparticles.

This process has the advantage of being simple to implement. The homogeneous distribution of the carboxylic acid or carboxylate groups within the microgel and the selection of nanoparticles that are positively charged at the surface makes it possible to encapsulate the nanoparticles within the microgel in a controlled manner, while preserving the colloidal and temperature-responsive properties of the final material.

The hybrid microgels of the invention may contain up to 50% by weight, in particular up to 35% by weight of nanoparticles without losing their colloidal, pH and temperature-responsive properties. The content of nanoparticles per hybrid microgels may be determined by thermogravimetric analysis (TGA).

The microgels described above optionally comprising nanoparticles are capable of self-assembling in order to form a film consisting of one or more layers of microgels, by a process of drying or evaporating an aqueous suspension of said microgels.

The films formed are cohesive and elastic. The microgels of the invention may thus be used as film-forming agent in cosmetic compositions, so as to improve the hold of these compositions on keratin materials. After drying, the films do not re-disperse when they are immersed in water.

The microgels and the films that they form may generate an electric potential via compression effect (Donnan effect). The films are prepared from microgels having ionic sites derived from carboxylate (COO⁻) functions. These ionic sites are constrained in the structure and create polarizations within the microgel (e.g. polyelectrolyte microgels). When the film is subjected to a pressure, a movement of the counterions helps to create a polarization within the film that generates an electric potential difference between the surface and the bulk of the film. The inventors have found that the presence of methacrylic acid improves the electromechanical properties of the films.

The self-assembly of monodisperse microgels also enables a diffraction of light thus generating a color. The photonic properties may be adjusted by the very composition of the microgels.

The monodisperse microgels of the invention may self-assemble periodically in the form of colloidal crystals. This particular self-assembly enables the diffraction of incident light and thus generates a color that can be observed depending on the viewing angle. This effect varies as a function of the composition of the microgels: a) the drying of a dispersion of microgels without nanoparticles induces the formation of a completely transparent colorless dry film that does not diffract light. Whereas this same film diffracts light in the wet state with colors that can be observed in solution, b) the drying of a dispersion of microgels containing magnetic nanoparticles (hybrid microgels) leads to the formation of a transparent, colored (brown) dry film that diffracts light. Consequently the film is brown at a viewing angle of 90° (color derived from the magnetic nanoparticles) and changes color in reflection at smaller viewing angles.

The presence of magnetic nanoparticles within the microgels makes it possible to orient the microgels with the aid of a permanent magnet and to improve the mechanical properties of the films. During the drying on a given surface, the temperature-responsive and magnetic microgels may be guided to and concentrated at a precise point with the aid of a permanent magnet. This has the effect of varying the thickness and the color of the films (darker or lighter brown tint). Furthermore, the magnetic nanoparticles improve the mechanical properties of the films in a wet medium thus making it possible to exert greater compression on the film.

All of these properties make it possible to envisage the use of the microgels of the invention and of the films that they form for the preparation of cosmetic or pharmaceutical products. These products may stimulate the skin by generating an electric current and optionally delivering a biologically active molecule via compression effect. The biologically active molecule may be encapsulated in microgels or be present in the product.

Another subject of the invention is therefore a cosmetic or pharmaceutical product consisting of or containing the microgels as described above and optionally at least one compound chosen from the group consisting of surfactants, oils, biologically active products, pigments and dyes.

The microgel of the invention may contain all sorts of ingredients or excipients used in the cosmetic and pharmaceutical field, preferably pigments based on iron oxide or biologically active substances.

The microgels of the invention may be synthesized by a precipitation polymerization process, using monomers pre-dissolved in aqueous solution.

The present invention also relates to a process for the precipitation polymerization of a polyethylene glycol) methacrylate microgel as described above, comprising a step of bringing into contact in the aqueous phase, in the presence of a crosslinking agent, the three monomers described above, at a temperature of between 40° C. and 90° C. The process of the invention does not require the presence of a surfactant such as SDS (dodecyl sulfate sodium).

The polymerization of the monomers may be initiated by addition of a water-soluble radical initiator, for example potassium persulfate (KPS) at a temperature of between 40° C. and 90° C., preferably of the order of 70° C.

It is preferred to add an aqueous solution of the monomer of formula $CR_1R_2=CR_3R_4$ gradually into an aqueous solution of the two other monomers, so as to guarantee the homogeneous distribution of the —COOH groups in the microgels that precipitate.

At the polymerization temperature, the polymer formed is hydrophobic and precipitates in the aqueous reaction medium in the form of spherical particles, the presence of the crosslinker OEGDA during the polymerization makes it possible to set the particles in this spherical shape by creating crosslinking points.

The microgels of the invention have the advantage of being of homogeneous structure, since the —COOH groups and the crosslinking points are uniformly distributed throughout their volume.

The microgel films are advantageously prepared by a process of drying or evaporating solvent at 20° C., for example by starting from a colloidal dispersion of monodisperse microgels at a weight concentration that may vary from 1.4 to 5 wt % in water.

According to this process, at least a first volume of solution may be left to dry until the complete evaporation of the water at ambient temperature. This step may be repeated several times in order to obtain a film composed of several layers of monodisperse microgels and having a thickness that may vary between 350 and 450 micrometers in the dry state.

The invention also relates to i) a cosmetic or pharmaceutical product consisting of or containing the microgels as described above and optionally at least one compound chosen from the group consisting of surfactants, oils, biologically active products, pigments and dyes, 2) a kit comprising a magnet and a cosmetic product containing microgels that is described above and that comprises magnetic nanoparticles, said magnet and said product being packaged together, iii) a cosmetic makeup or care process that consists in applying to the skin microgels or a cosmetic product described above, iv) a thin-film comprising at least one layer of microgels or of hybrid microgels described above, and v) the uses thereof in various fields of application such as optics, electronics, sensors, cosmetics, pharmacy and medical diagnosis.

BRIEF DESCRIPTION OF THE FIGURES

FIG. 14 depicts Table 1, which shows compositions and morphologies of microgels used to prepare films in Example 4.

Figure 1:
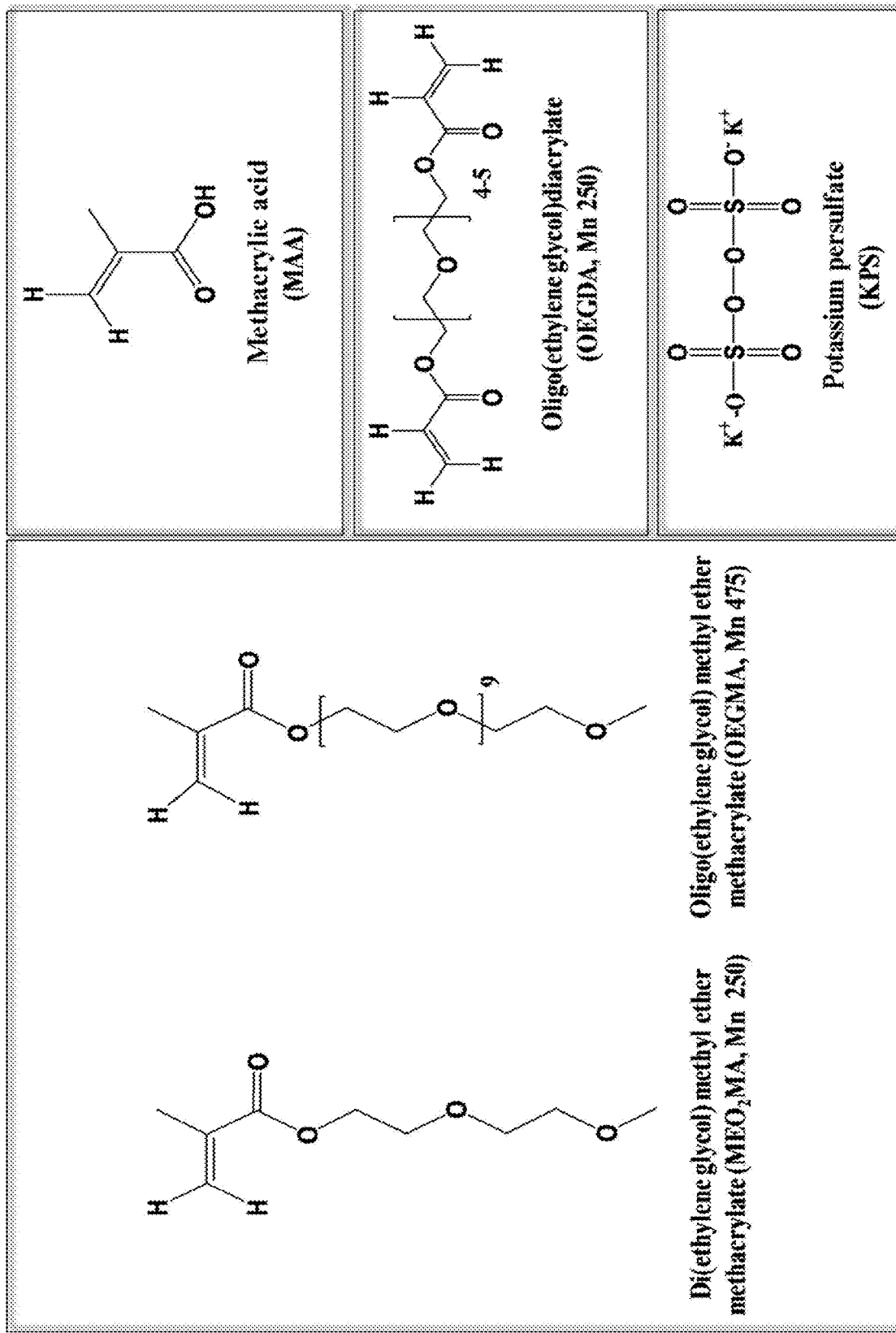
FIG. 1 presents the chemical structures of the monomers used for the synthesis of the biocompatible microgels of the invention.
Figure 2:
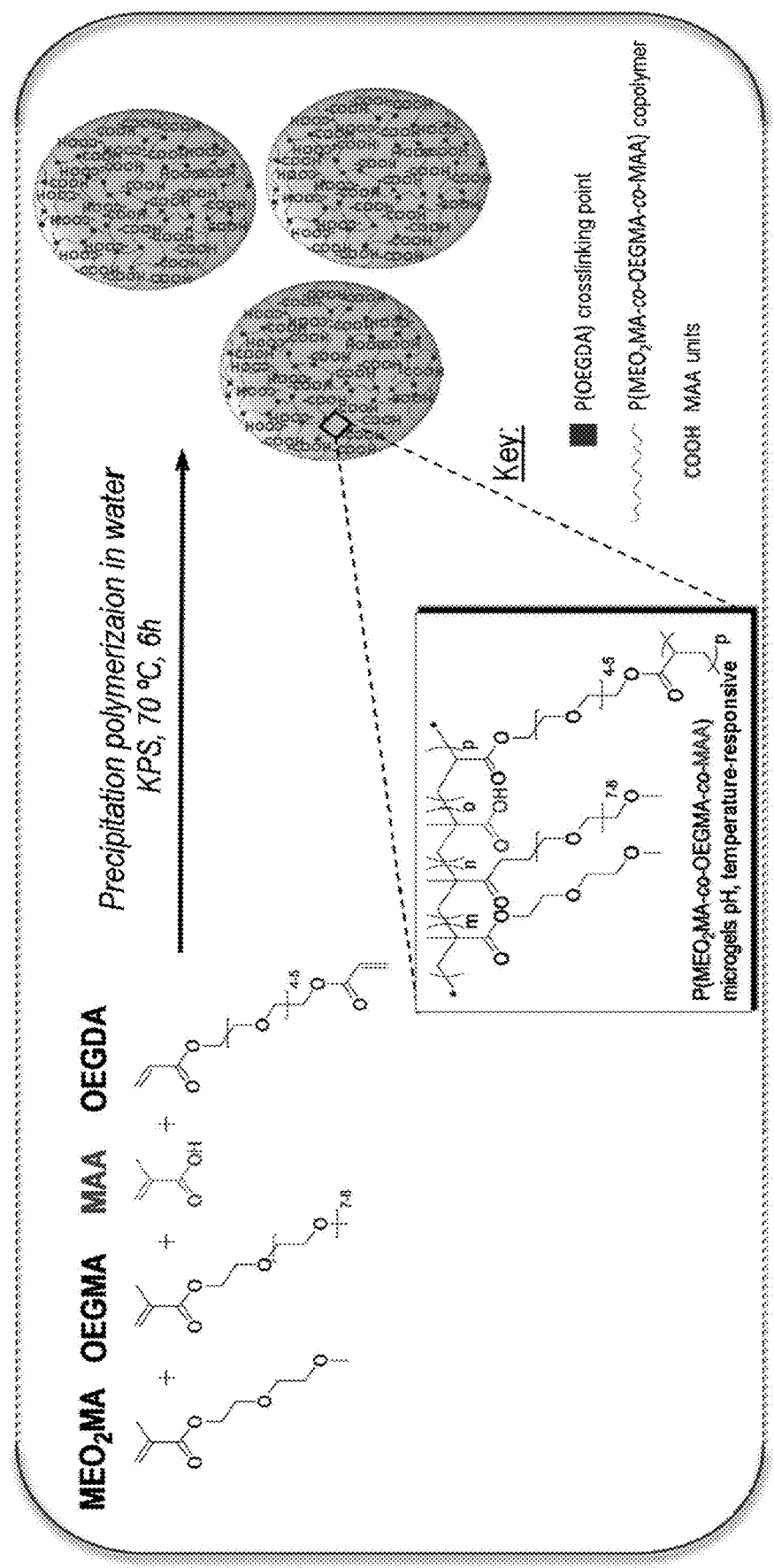
FIG. 2 is a synthetic scheme of the pH-responsive and temperature-responsive biocompatible microgels based on poly(MEO$_2$MA-co-OEGMA-co-MAA) of the invention.
Figure 3:
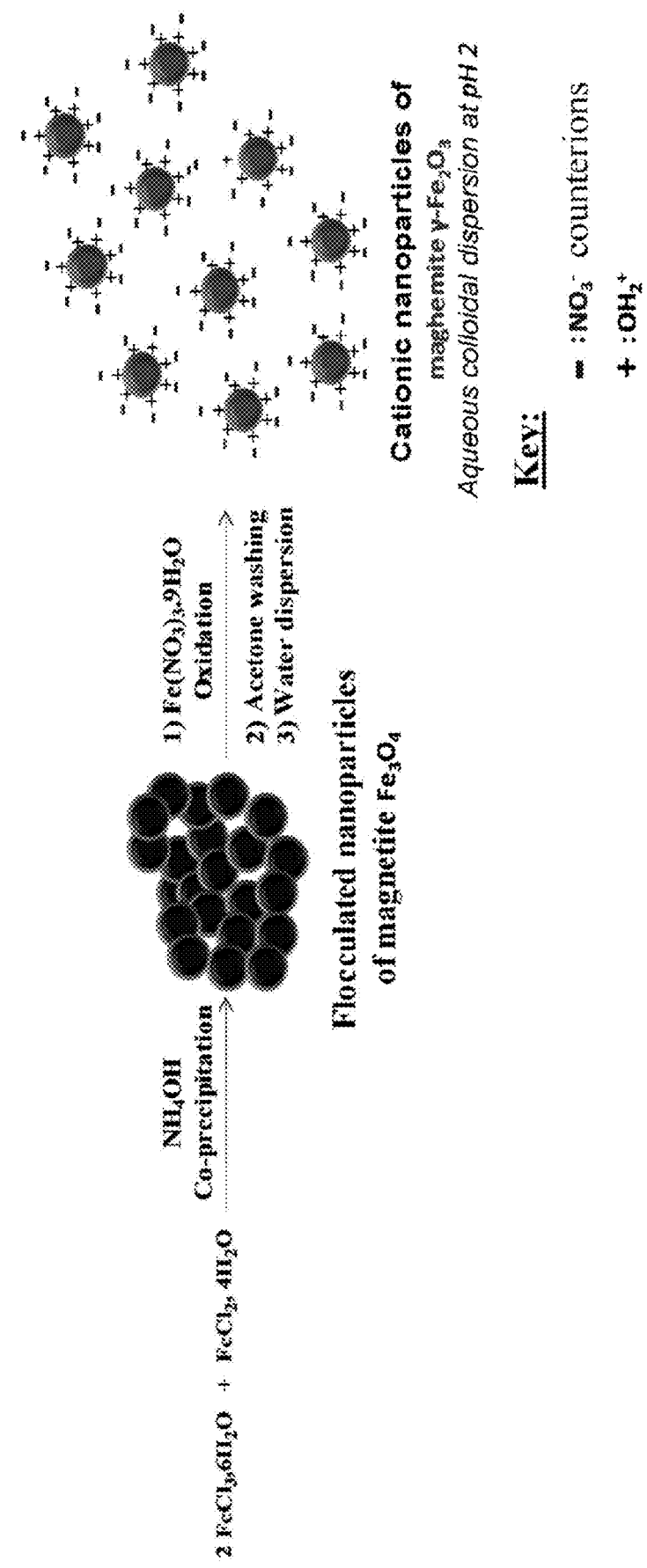
FIG. 3 is a scheme for preparing $\gamma$-Fe$_2$O$_3$ particles.

The invention is also illustrated by the following examples.

EXAMPLE 1

Synthesis of a Microgel Based on Poly(Oligo(Ethylene Glycol)Methacrylate) According to the Invention The following monomers were used: di(ethylene glycol) methyl ether methacrylate (M(EO)$_2$MA, Mn 250 g.mol$^{-1}$), oligo(ethylene glycol) methyl ether methacrylate (denoted OEGMA hereinafter, Mn 475 g.mol$^{-1}$), and methacrylic acid (MAA). The crosslinking agent was oligo(ethylene glycol) diacrylate (OEGDA, Mn 250 g.mol$^{-1}$).

Experimental Protocol:

0.966 g of MEO$_2$MA (5.14×10$^{-3}$ mol), 0.272 g of OEGMA (5.73×10$^{-4}$ mol) and 0.029 g of OEGDA (1.17× 10$^{-4}$ mol) are introduced into a volume of 57.5 mL of water and left under magnetic stirring until the monomers have completely dissolved. The mixture is then filtered and introduced into a three-necked flask having a volume of 250 mL that is equipped with a mechanical stirrer before being degassed under nitrogen for 45 min with mechanical stirring (150 rpm). An aqueous solution of MAA (0.026 g, 3.05× 10$^{-4}$ mol dissolved in 2 mL of water) is then introduced into the reaction medium. The mixture is left at 70° C. for 20 min before introducing an aqueous solution of potassium persulfate (KPS, 0.0143 g dissolved in 2.5 mL of water) previously degassed under nitrogen. The addition of KPS makes it possible to initiate polymerization and the reaction medium is left under mechanical stirring (50 rpm) at 70° C. for 6 h.

The polymerization is then stopped by addition of oxygen and left to cool to ambient temperature. The microgels are then separated from the reaction medium by centrifugation (10 000 rpm, 30 min) and the reaction medium is replaced by pure water (of milliQ grade); the step is repeated five times.

The final solution is then composed of a colloidal dispersion of P(MEO$_2$MA-co-OEGMA-co-MAA) microgels in the aqueous phase, this dispersion is kept at ambient temperature.

Property of the Microgel

The synthesis of the microgels was characterized by kinetic monitoring of the monomers using proton nuclear magnetic resonance ($^1$H NMR) spectroscopy. A complete conversion of the monomers and also a homogeneous composition of the microgels, with a homogeneous distribution of the crosslinking points and of the methacrylic acid units, are observed.

The final yield of crosslinked microgel was analyzed by solids content of the reaction medium and makes it possible to determine a yield of 70 wt % of crosslinked microgel.

The content of methacrylic acid incorporated was determined by acid-base titration of the purified microgels. The pH-responsive nature of the microgels in aqueous solution and also the incorporation of 70 mol % of the initial MAA monomer were able to be verified.

The microgels were observed by transmission electron microscopy (TEM) and their sizes were determined by dynamic light scattering. The microgels observed are monodisperse, with a size of 400 nm in the dried state and that may range up to 1000 nm in the wet state.

EXAMPLE 2

Preparation of Solutions of a Microgel Based on Poly(Oligo(Ethylene Glycol) Methacrylate)

1.2 mL of a solution of microgels prepared according to Example 1 (containing 15 g.L$^{-1}$ of microgels) are dispersed in 10 mL of a solution of pure water (milliQ grade). The pH of the dispersion is adjusted by addition of a 0.1 mol.L$^{-1}$ solution of hydrochloric acid or of potassium hydroxide. The mixture is left under magnetic stirring until the pH has stabilized. The size of the microgels in solution is measured by dynamic light scattering and the temperature of the solution is controlled during the analysis.

By studying the size of the microgels in solution by dynamic light scattering, it was possible to evaluate the impact of the pH and of the temperature of the medium on the capacity of the microgels to swell or to shrink in water.

The microgels are responsive to pH variations of the medium, changing from a size of 400 nm at pH<5.5 to a size of 1000 nm at pH>6.0.

The microgels are temperature-responsive and change from a swollen state at 20° C. to a shrunken state at high temperature. The shrinkage temperature depends on the pH (35° C. at pH<6.0 and 55° C. at pH>7.0). Finally, the volume of the swollen microgel at 20° C. decreases up to 3 times relative to its initial volume when the temperature goes beyond the shrinkage temperature.

EXAMPLE 3

Preparation of a Microgel Based on Poly(Oligo(Ethylene Glycol) Methacrylate) Containing Magnetic Nanoparticles Synthesis of the maghemite γ-Fe$_2$O$_3$ nanoparticles The reactants used are: ferrous chloride tetrahydrate (FeCl$_2$.4H$_2$O), ferric chloride hexahydrate (FeCl$_3$.6H$_2$O), 28-30% w/w ammonium hydroxide (NH$_4$OH), iron nitrate (Fe$^{III}$(NO$_3$)$_3$.9H$_2$O), 36% v/v hydrochloric acid (HQ) and nitric acid (HNO$_3$).

The maghemite nanoparticles used during this study were synthesized by coprecipitation of the metal salts (Fe$^{II}$ and Fe$^{III}$). This method of synthesis consists in forming nanoparticles of magnetite (Fe$_2$O$_3$) by coprecipitation of ferrous chloride (FeCl$_2$) and ferric chloride (FeCl$_2$) in a basic medium by addition of ammonium hydroxide (NH$_4$OH). The magnetite is then oxidized to form the maghemite (γ-Fe$_2$O$_3$) variety. The oxidation of the magnetite to maghemite makes it possible to establish pH-responsive hydroxyl functions at the surface of the nanoparticles, these functions having a point of zero charge at a neutral pH (pH≈7.2). Thus, at acidic or basic pH values, these nanoparticles have a colloidal state in the aqueous phase by electrostatic repulsion of anionic charges (at basic pH) or cationic charges (at acidic pH). This is a versatile method for synthesizing magnetic nanoparticles that are stabilized in the aqueous phase, commonly referred to as "cationic ferrofluids" or "anionic ferrofluids" depending on the pH of stabilization.

Experimental Protocol

Step 1: Formation of the Magnetite 12.2 g of ferric chloride hexa hydrate FeCl$_3$.6H$_2$O (0.0451 mol) are introduced into a 3 L beaker containing 500 mL of pure water. 4.49 g of ferrous chloride tetrahydrate $FeCl_2 \cdot 4H_2O$ (0.0226 mol) are dissolved in 24.3 mL of a 1.5 $mol.L^{-1}$ solution of hydrochloric acid (HCl) is added to the 3 L beaker and everything is left mixing under gentle mechanical stirring (initial $Fe^{II}/Fe^{III}$ ratio=0.5). A volume V=43 mL of 28/30% w/w ammonium hydroxide is then added to the beaker with vigorous mechanical stirring and at ambient temperature. The addition of ammonium hydroxide leads to the formation of flocculated magnetites ($Fe_2O_3$) in basic aqueous solution (pH>10), the magnetite flocs are then left to settle under the effect of a magnetic attraction generated by a permanent magnet, then the supernatant is removed and replaced by pure water (milliQ grade). The washing step is repeated twice in order to remove the excess ammonium hydroxide.

Step 2: Desorption of the Ammonium Counterions and Surface Oxidation

After the successive steps of washing the magnetite, a volume V=28.6 mL of a 2 $mol.L^{-1}$ aqueous solution of nitric acid $HNO_3$ is added to the magnetite flocs and is left under mechanical stirring for 30 min in order to treat the surface of the magnetite particles.

The addition of nitric acid makes it possible to acidify the medium and to induce a desorption of the excess ammonium $NH_4^+$ counterions at the surface of the nanoparticles by ion exchange with the nitrate $NO_3^-$ ions. The oxidation of the particles at the surface also makes it possible to dissolve the ferrous ions that have not precipitated and that are present at the surface of the nanoparticles.

The surface-treated magnetite flocs are left to settle under a permanent magnet, then the supernatant is removed and replaced by pure water, this step is repeated twice.

Step 3: Oxidation of the Core of the Nanoparticles

After the successive steps of washing the surface-treated magnetites, a volume V=85.7 mL of a freshly prepared 0.33 $mol.L^{-1}$ solution of ferric nitrate $Fe^{III}(NO_3)_3 \cdot 9H_2O$ is added at boiling to the magnetite flocs and is left under reflux and under mechanical stirring for 45 min.

The introduction of the $Fe^{3+}$ ions by the ferric nitrate makes it possible to oxidize the $Fe^{II}$ of the particles thus forming the maghemite $\gamma$-$Fe_2O_3$ variety. After complete oxidation of the particles, the maghemite floc is left to settle under permanent magnet and the supernatant is removed then replaced by pure water, the operation is repeated twice.

Step 4: "Peptization" of the Magnetite Nanoparticles

A volume V=28.6 mL of a 2 $mol.L^{-1}$ solution of nitric acid $HNO_3$ is added to the maghemite floc and left at ambient temperature and under mechanical stirring for 30 min. The addition of nitric acid makes it possible to introduce hydronium $H^+$ ions at the surface of the maghemite. The cationic maghemite floc is left to settle then washed three times with acetone. A volume V=70 mL of water is then added to the nanoparticles enabling a "peptization" of the nanoparticles in the water, the dispersion of nanoparticles is then stabilized by electrostatic repulsion of positive charges at the surface of the nanoparticles. Lastly, the residual acetone is removed by evaporation under vacuum at 40° C.

Synthesis of P($MEO_2MA$-Co-OEGMA-Co-MAA)/$\gamma$-$Fe_2O_3$ Hybrid Microgels

Figure 4:
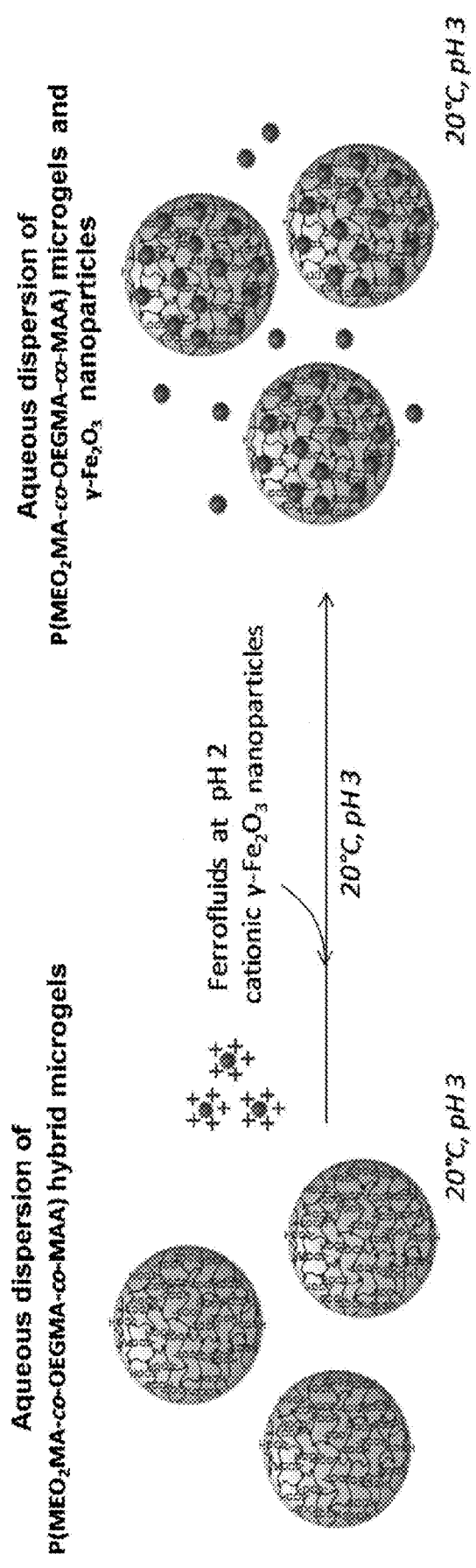
FIGS. 4 and 5 are schematic representations respectively of the 1$^{st}$ and of the 2$^{nd}$ synthesis step of the process for preparing hybrid microgels according to the invention containing $\gamma$-Fe$_2$O$_3$ particles.

The hybrid microgels are synthesized by simple mixing of an aqueous dispersion of P($MEO_2MA$-co-OEGMA-co-MAA) microgels with a dispersion of maghemite nanoparticles that is stabilized at pH 2 (nanoparticles with cationic charges). The encapsulation of the nanoparticles within the microgels is carried out in 2 steps:

A first step consists in adding the cationic nanoparticles to a solution of microgels dispersed at pH 3 and at ambient temperature. These mixing conditions make it possible to retain the cationic charge at the surface of the $\gamma$-$Fe_2O_3$ nanoparticles. The nanoparticles will preferentially interact with the microgels owing to the carboxylic acid groups resulting from the methacrylic acid units contained within the microgels. Specifically, the carboxylic acid groups have the ability to be adsorbed at the surface of particles of metal oxide such as iron oxide and furthermore the positive charge at the surface of the nanoparticles enables a favored interaction. In this sense, upon addition of $\gamma$-$Fe_2O_3$ nanoparticles, the latter will preferentially be located within the microgels (step summarized in FIG. 4).

Figure 5:
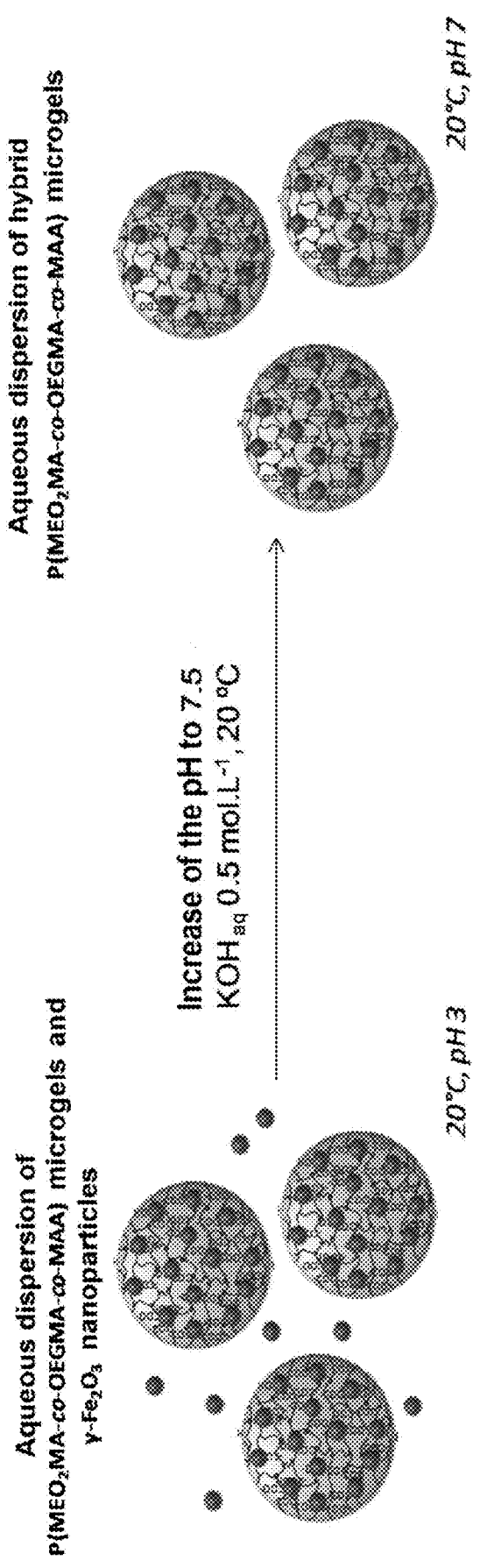

A second step consists in increasing the pH of the medium (microgels+nanoparticles) starting from pH 3 up to pH 7.5. This rise in the pH induces: 1) A destabilization of the cationic $\gamma$-$Fe_2O_3$ nanoparticles within the mixture. Specifically, since the nanoparticles have a point of zero charge at neutral pH (isoelectric point=7.2), the latter flocculate at this pH due to lack of electrostatic repulsion. 2) The creation of negative charges within the microgels derived from the carboxylic acid (COOH) functions in the form of carboxylate ($COO^-$) groups. The concomitance of these two phenomena makes it possible to anchor the magnetic nanoparticles within the microgel and to improve the stability of the hybrid microgels owing to the negative charges of the carboxylate functions (step summarized in FIG. 5).

Experimental Protocol

A volume of 40 mL of an aqueous dispersion of P(($MEO_2MA$-co-OEGMA-co-MAA) microgels having a weight concentration of 1.45 $g.L^{-1}$ is introduced into a 100 mL round-bottomed flask and left under magnetic stirring, the pH of the dispersion is adjusted to 3.0 by addition of a 0.1 $mol.L^{-1}$ solution of nitric acid ($HNO_3$). Next, a volume of 10 mL of a dispersion of cationic magnetite nanoparticles at pH 3 having a weight concentration of 1.34 $g.L^{-1}$ is added dropwise to the mixture at ambient temperature and under magnetic stirring, this corresponds to an amount of nanoparticles per hybrid microgels of ~18.8%. The reaction mixture is left under stirring and at ambient temperature for 12 h. The pH of the reaction mixture is then increased by dropwise addition of a 0.5 $mol.L^{-1}$ solution of potassium hydroxide (KOH). Finally, the hybrid microgels are separated from the reaction medium by centrifugation (5000 rpm, 20 min) and the reaction medium is replaced by pure water (of milliQ grade). The final solution is then composed of a colloidal dispersion of P(($MEO_2MA$-co-OEGMA-co-MAA) microgels in water, this dispersion is kept at ambient temperature. Various syntheses have been carried out by varying the theoretical weight fraction of nanoparticles per hybrid microgel between 0 and 33%.

Property of $\gamma$-$Fe_2O_3$/P($MEO_2MA$-Co-OEGMA-Co-MAA) Hybrid Microgels

The hybrid microgels were characterized in the dry state by transmission electron microscopy (TEM) and in the wet state by dynamic light scattering. The hybrid architecture of the microgels was demonstrated by TEM, the observation of the microgels in the dry state makes it possible to reveal the good encapsulation of the magnetic nanoparticles within the microgels which are not expelled during the drying treatment. The content of nanoparticle fillers encapsulated was determined by thermogravimetric analysis, the analysis confirms a quantitative and significant encapsulation of the nanoparticles (filler contents tested ranging from 0 to 33 wt % of nanoparticles per hybrid microgel). The temperature-responsive properties of the hybrid microgels in aqueous solution at neutral pH are also demonstrated with a shrinkage of the hybrid microgels which change from 1000 nm at 20° C. to 450 nm with a shrinkage temperature of 37° C. This shrinkage at neutral pH takes place regardless of the magnetic nanoparticle filler content.

EXAMPLE 4

Films of Microgels

The compositions of microgels summarized in Table 1 of FIG. 14 are used to prepare the films.

Figure 6:
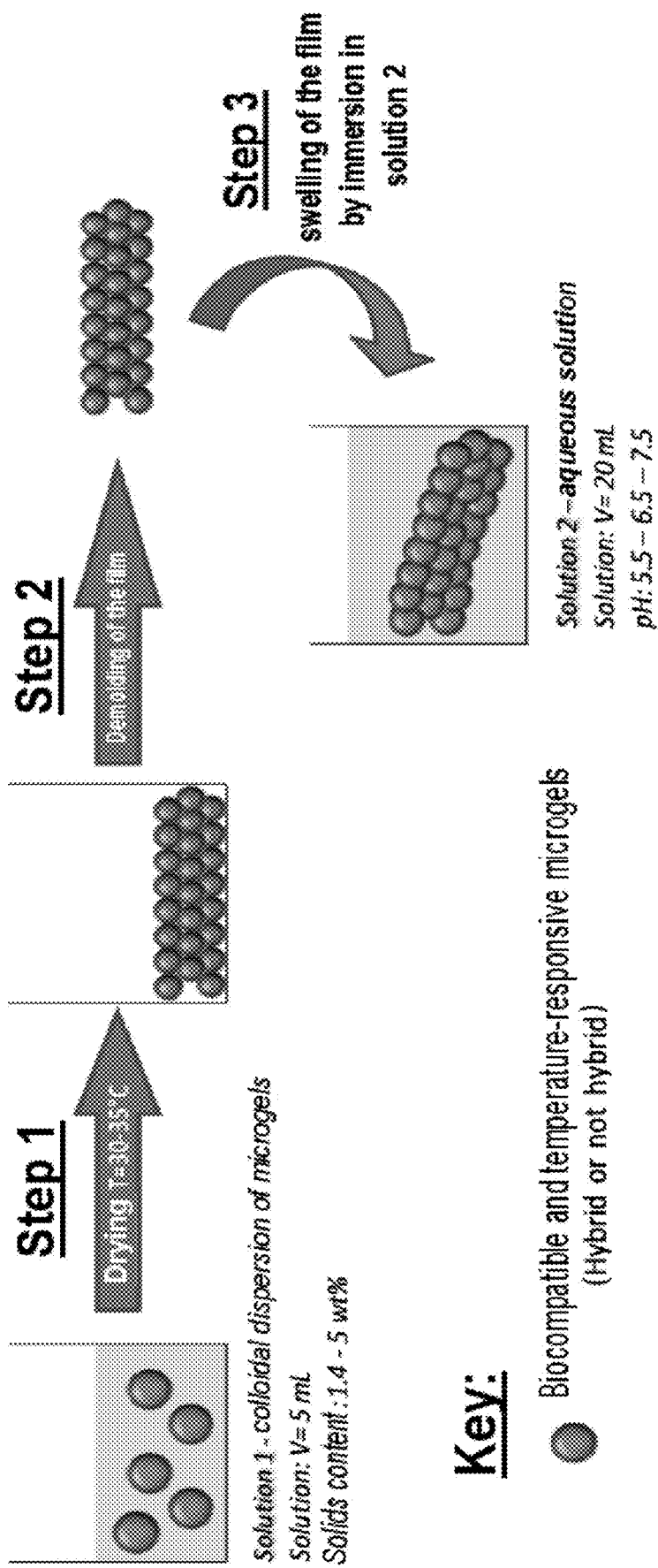
FIG. 6 represents a scheme of the process for forming films of microgels according to the invention.

The films are prepared by a drying process presented in FIG. 6, starting from a colloidal dispersion of monodisperse microgels (having a size that may vary between 500 and 1000 μm in solution) having a weight concentration of microgels that varies from 1.4 to 5 wt % in water (solution 1). A constant volume of solution is introduced into a plastic mold and left to dry until the water has completely evaporated (step 1 from FIG. 6). The film remaining at the bottom of the mold is then composed of several layers of monodisperse and completely dry microgels (having a size that may vary between 350 and 450 μm in the dry state). The film is carefully recovered and reintroduced into an aqueous solution (solution 2). Various parameters are varied: 1.) The weight concentration of dispersion from 1.4 to 5 wt % makes it possible to vary the swollen film thickness (end of step 3: thickness from 200 μm to 1000 μm). 2.) The pH of solution 2 is varied between 5.5 and 7.5.

Experimental Protocol: Formation of the Films of Temperature-Responsive Microgels Based on Poly(Oligo(Ethylene Glycol) Methacrylate)

A volume of 5 mL of a colloidal dispersion of microgels at a weight concentration of 1.4 to 5 wt % is introduced into a plastic mold and left to dry at a temperature of 32° C. (+/−2° C.). After complete evaporation of the solvent, the film is carefully recovered then introduced into an aqueous solution and left to swell at ambient temperature.

The recovered films were observed by atomic force microscopy in the dry state and characterized using a rheometer in the wet state (end of step 3 of FIG. 6). The microgels form an elastic film composed of several layers of microgels (step 2) and this being irrespective of the composition of the microgels (microgels 1 to 5 in table 1). Conversely, the microgels lose their mechanical properties when they are swollen in water but do not re-disperse in solution.

Microgels 1 and 2: the film thickness is varied from 200 to 1000 μm, the multiplication of the layers of microgels does not modify the "film formation" phenomenon and the films keep their elasticity in the dry state.

Microgels 3, 4 and 5: A thickness of the order of 300 μm (swollen films in step 3) were studied in the case of the hybrid microgels. The addition of nanoparticles does not modify the film-forming properties of the microgels. On the contrary, the mechanical properties of the films are greatly improved in the wet state.

Evaluation of the Electromechanical Properties of the Films

1. Characterisation of the Electromechanical Properties of the Films

The electromechanical properties of the films of microgels were studied. This is a question of demonstrating the capacity of the microgels to generate an electric current when a pressure is exerted on these microgels. More particularly, the idea of the invention is to generate an electric current by pressing the material at the surface of a substrate. This electric potential may be generated from a material having ionic functions attached covalently (or polyelectrolyte material). Specifically, since the ionic groups are attached in the microgel, only the counterions of each carboxylate group have a mobility in the microgel. When a unidirectional pressure/deformation is exerted on these polyelectrolyte microgels, the mobility of the counterions is favored, thus creating a polarization between the positive charges of the mobile counterions and the negative charges of the attached carboxylate groups. This ionic gradient results in an electric potential at the interface. Thus, the presence of ionizable functions in the microgel would make it possible to create a polarization within the material and to generate an electric potential.

Figure 7:
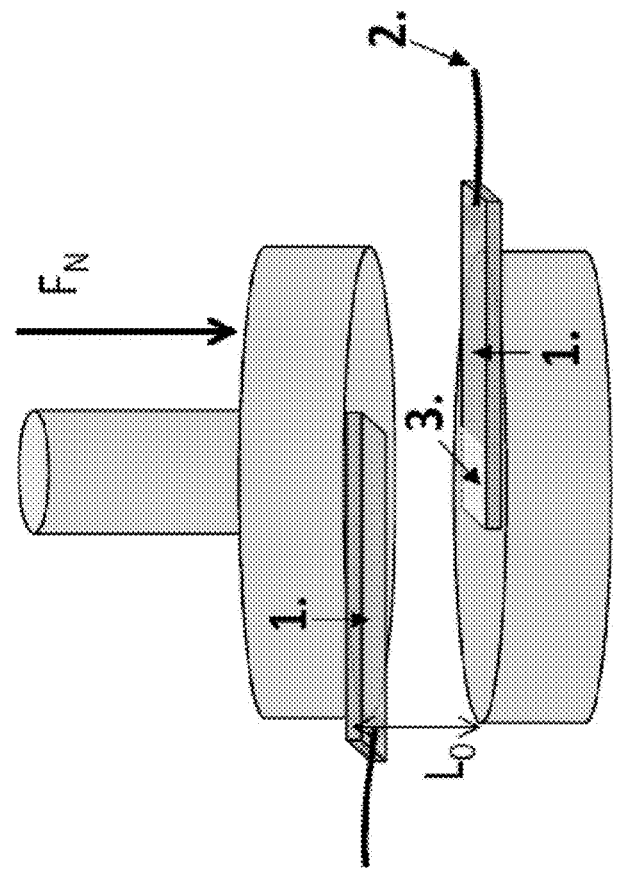
FIG. 7 represents an assembly for characterizing the electromechanical effect of the films of microgels of the invention.

An assembly is used in order to demonstrate the electromechanical properties of the films. For this, an Anton Paar MCR301 rheometer is used in plate-plate geometry within which two flat and conductive electrodes based on indium tin oxide or ITO (entity 1. from FIG. 7) are attached on either side of the geometry. The lower electrode is fixed and the upper electrode is removable. A wet film of microgels (entity 3. from FIG. 7) is deposited on the surface of the lower electrode and the upper electrode is lowered in order to exert a compression of force $F_N$ on the film. By controlling the distance between the two electrodes, it is possible to control the crushing force ($F_N$) exerted on the film.

Figure 8:
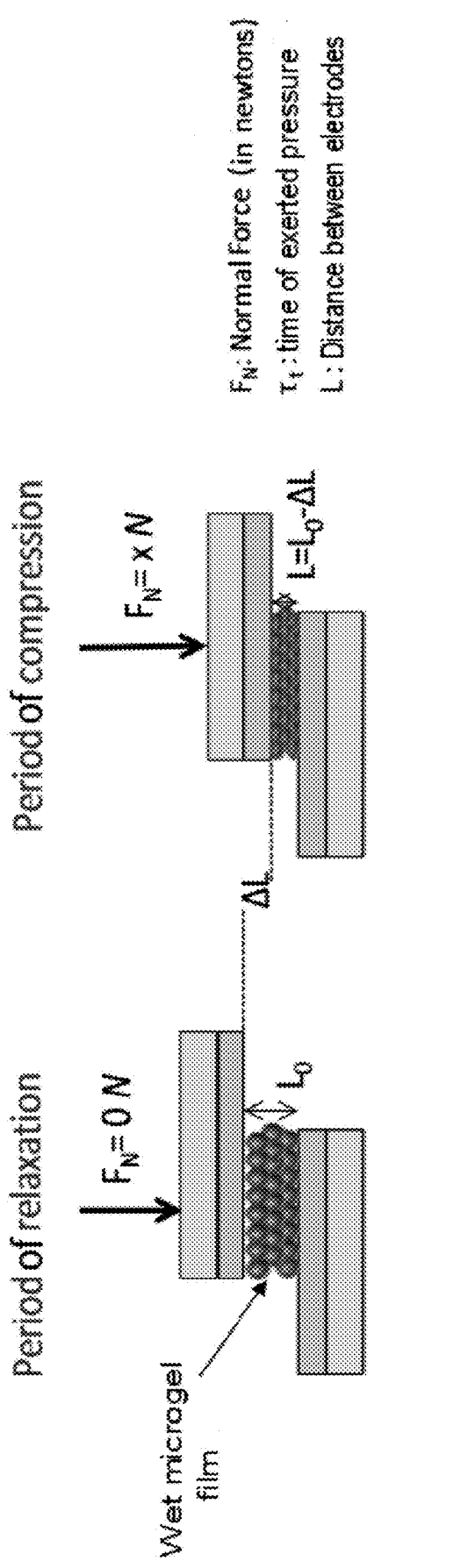
FIG. 8 is a schematic representation of the period of compression and relaxation of a film de microgels of the invention.

A program of compression/relaxation is carried out in order to vary the force exerted on the film. Firstly, the initial thickness of wet film (denoted $L_0$) was determined and the distance between the two electrodes was gradually reduced by a distance $\Delta L$ by lowering the upper electrode. The program is distinguished by a short period of crushing ($\tau=2$ seconds) with a final distance L then a long period of relaxation ($\tau=20$ seconds) with a return to the initial state $L_0$, everything making it possible to simulate a "touch-sensitive" type action on the film (FIG. 8).

In the crushing period, a normal force $F_N$ (in newtons) is recorded. This force $F_N$ is proportional to the crushing thickness ($\Delta L$). The program is arranged as such: the film is compressed to a distance $L=L_0-\Delta L$ with $\Delta L=(3\times)$ 10%.$L_0$, then $(3\times)$ 20%.$L_0$, then $(3\times)$ 25%.$L_0$ etc. An example of a program used is given in FIG. 9.

Lastly, the upper and lower electrodes are connected to a converter/amplifier, in order to record the potential difference (denoted E) generated between the two electrodes throughout the program.

2. Study of the Films of Microgels

Films of P(MEO$_2$MA-Co-OEGMA-Co-MAA) Microgels

Figure 9:
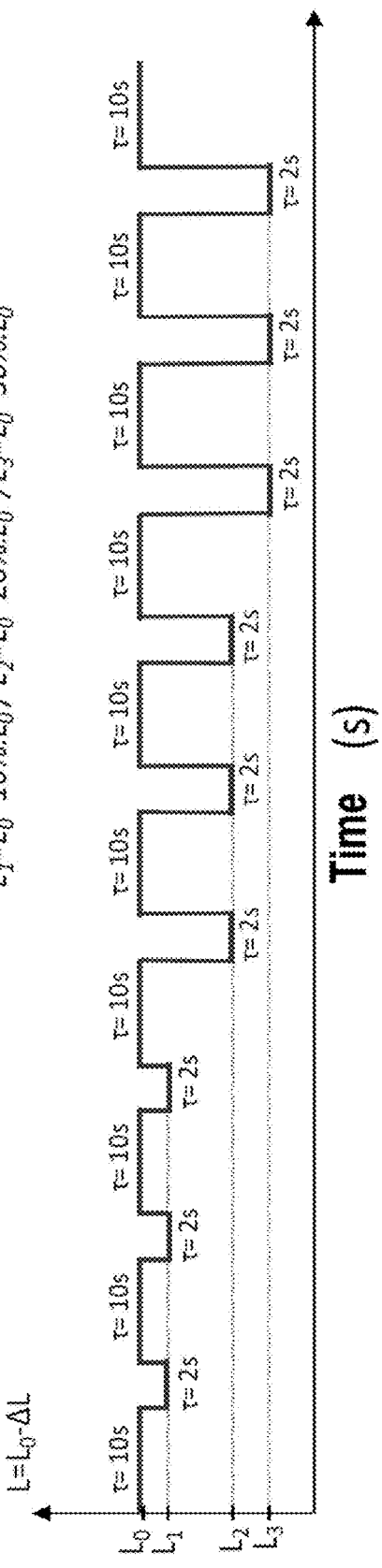
FIG. 9 represents the diagram of a compression and relaxation program of microgels of the invention.
Figure 9:
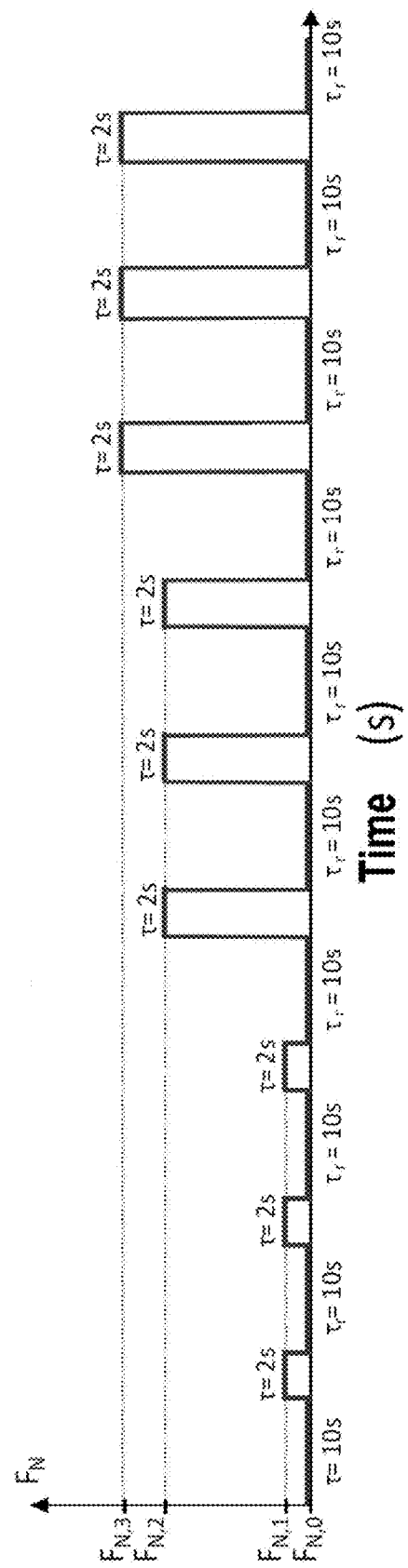

The films of P(MEO$_2$MA-co-OEGMA-co-MAA) biocompatible microgels were characterized by varying 3 parameters:

1.) The effect of the multiplication of the compressions: for each film, a compression of the same force is repeated successively (3 times as represented in FIG. 9) and the potential of each compression is analyzed.

2.) Rim thickness: two film thicknesses were tested in order to determine the impact of the thickness on the ability of the films to generate an electric potential at the interface (~200 μm and ~900-1000 μm).

3.) Composition of carboxylic acid functions: the composition of MAA units was varied from 0 to 3.5 mol % of MAA (microgels 1 and 2) in order to evaluate the impact of the MAA units on the electric potential.

4.) The pH of the solution in which the films are swollen: the pH makes it possible to vary the amount of ionic functions (COO⁻) within the microgel. Specifically, the carboxylic acid functions are present in the form of two protonated (COOH) and deprotonated or ionized (COO⁻) species. The proportion of these two species depends on the pH of the solution with an increase in the ionized species COO⁻ when the pH is increased (pH 5.5→% COO⁻=0; pH 6.5→% COO⁻=50%; pH 7.5→% COO⁻=75%).

TABLE 1

Summary of the samples studied.

| Sample | MAA (mol %) | γ-Fe$_2$O$_3$ (wt %) | Thickness of swollen film (μm) | pH | $E_{max}$ (mV) | $F_N$ (N) |
|---|---|---|---|---|---|---|
| Effect of the film thickness | | | | | | |
| Microgel 2 | 3.5 | 0 | 180 | 6.5 | 5.4-11.1 | 0.38-0.40 |
| Microgel 2 | 3.5 | 0 | 850 | 6.5 | 2.0-5.6 | 0.30-0.35 |
| Effect of the MAA composition | | | | | | |
| Microgel 1 | 0 | 0 | 275 | 6.5 | 0.43-0.9 | 0.30-0.35 |
| Microgel 2 | 3.5 | 0 | 180 | 6.5 | 5.4-11.1 | 0.38-0.40 |
| Effect of the pH | | | | | | |
| Microgel 2 | 3.5 | 0 | 310 | 5.5 | 2.0-9.9 | 0.7-0.9 |
| Microgel 2 | 3.5 | 0 | 180 | 6.5 | 5.4-11.1 | 0.38-0.40 |
| Microgel 2 | 3.5 | 0 | 350 | 7.5 | 5.5-11.2 | 0.18-0.23 |
| Effect of γ-Fe$_2$O$_3$ | | | | | | |
| Microgel 2 | 3.5 | 0 | 180 | 6.5 | 5.4-11.1 | 0.38-0.40 |
| Microgel 2 | 3.5 | 4.7 | 310 | 6.5 | 8.7-12.2 | 0.65-1.13 |
| Microgel 2 | 3.5 | 9.1 | 320 | 6.5 | 2.4-3.7 | 1.0-1.2 |
| Microgel 2 | 3.5 | 16 | 180 | 6.5 | 3.7-3.8 | 3.0-3.1 |

Results:

By observing the change in the electric signal during the compression of the films of microgels, an electromechanical effect is demonstrated over all of the films characterized. This electromechanical effect is a function of the force $F_N$ exerted on the films with an electric potential that increases with the compression force. Furthermore, a trend seems to emerge as a function of the analysis parameters:

Effect of the repetition of the compressions: the electric potential recorded is very high during the first compression. Whilst during the $2^{nd}$ and $3^{rd}$ compression, the potential generated is lower. This first observation may be due to a significant movement of the ions in the first compression of the film creating a high instantaneous electric potential (~12 mV). After a relaxation time of 20 s, the following compressions of the same force do not appear sufficient to bring about this same movement of the ions with a generated potential that decreases.

Effect of the film thickness: the electric potential generated by the compression of the films of different thicknesses shows a weak electromechanical effect when the film is too thick (E=2-5.6 mV for $F_{N,max}$=0.35 N). Conversely, a greater electromechanical effect is seen when the film thickness is small ranging from 11 to 5 mV for forces $F_N$ of 0.38 to 0.4 N. Too large a thickness would not therefore make it possible to have a sufficient impact on the mobility of the ions. (cf. Table 1. Effect of the film thickness)

Composition of carboxylic acid functions: the presence of methacrylic acid appears to improve the electromechanical properties of the films. Specifically, the films appear more sensitive to the compression effects with an electric potential measured for weak forces (11-5 mV at 0.4 N with MAA versus 1-0.5 mV at 0.4 N without MAA). Furthermore, the measurement made at pH 6.5 highlights the importance of the ionized carboxylate groups derived from the MAA units (50% of ionized MAA group) on the sensitivity of the films of microgels. (cf. Table 1. Effect of the MAA composition)

The pH of the solution from 5.5 to 7.5 on the films of microgels of the same composition does not appear to modify the electric potential value of the films but when the pH of the solution is increased, the loss of the electric potential in the face of the compression repetitions appears to be reduced. Specifically, at pH 5.5, the repetition of the compression makes the electric potential drop to 2 mV whereas at a higher pH, the potential drops to 5.4 mV. This is probably due to the increase in the proportion of the ionized carboxylate functions (% COO$_{pH5.5}$=0%; % COO$_{pH6.5}$=50%; % COO$_{pH 7.5}$=75%), increasing the polarization capacity of the microgels that form the film. The films are then more sensitive when the pH is increased, (cf. Table 1. Effect of the pH)

Films of P(MEO$_2$MA-Co-OEGMA-Co-MAA)/γ-Fe$_2$O$_3$ Hybrid Microgels

The films of hybrid microgels were characterized at pH 7.5 and were compared to a film of microgels without magnetic nanoparticles (NPs). A film of microgels without nanoparticles has a maximum potential of 6 mV for a compression force $F_N$=0.4 N. For the films of microgels with nanoparticles, the potential generated depends on the amount of nanoparticles incorporated:

For 5 wt % of magnetic nanoparticles incorporated, the nanoparticles have no effect on the electric potential generated and the response of the film to the compressions is 6-7 mV.

For 9 and 17 wt % of magnetic nanoparticles incorporated, a reduction of the electric potential, which reaches 2.5 mV irrespective of the compression force, is observed. This loss of electric potential may be attributed to the reduction of charges derived from the carboxylic acid units at pH 7.5 since they already interact with the NPs. Specifically, the incorporation of the nanoparticles takes place by adsorption of the latter at the ionic sites (COO⁻) contained in the microgels. This adsorption appears to reduce the fraction of ionic sites still available within the microgel and thus to reduce the polarization capacity of the microgels. An amount of 5 wt % of nanoparticles incorporated does not influence the polyelectrolyte behavior of the hybrid films (cf. Table 1. Effect of γ-Fe$_2$O$_3$).

Optical Properties of the Microgels

Besides the electromechanical properties, the films of microgels are distinguished by their optical properties, linked to the ability of these films to diffract light. A disparity is observed as a function of the composition of the films:

Films of P(MEO$_2$MA-Co-OEGMA-Co-MAA) Microgels

Figure 10:
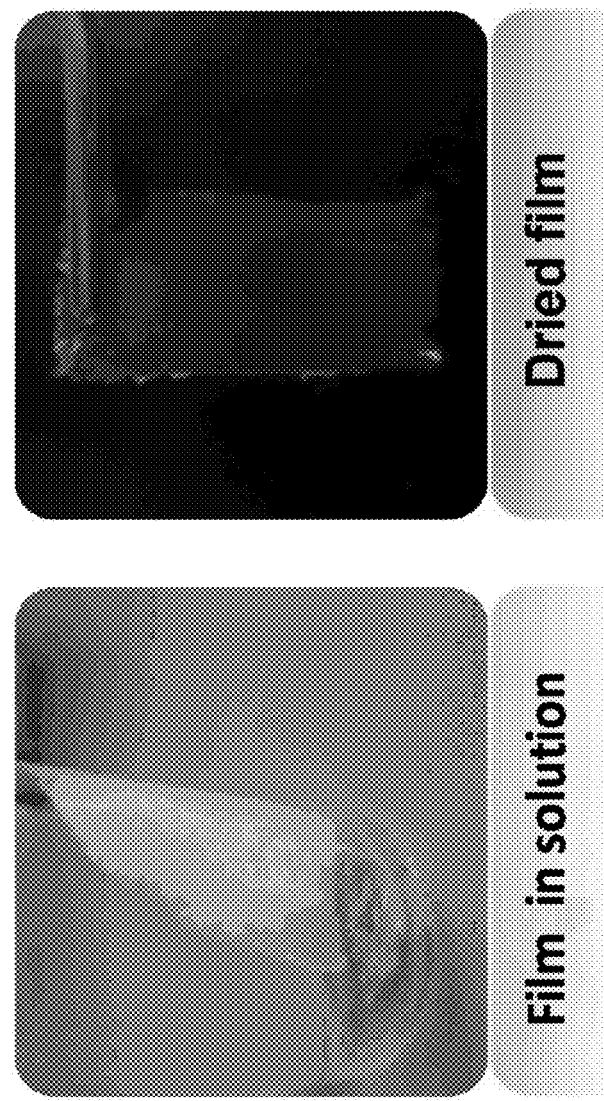
FIG. 10 is an image of films of microgels of the invention in the dry state and swollen in solution.

During the drying of a colloidal dispersion of microgels without nanoparticles, the films formed are transparent in the dry state and iridescent in the wet state (FIG. 10). It appears that during the swelling of the microgels, the diameter and the distance between the particles favor a diffraction of light in the visible region, this diffraction is demonstrated by the observation of photonic crystals.

Films of P(MEO$_2$MA-Co-OEGMA-Co-MAA)/γ-Fe$_2$O$_3$ Hybrid Microgels

Figure 11:
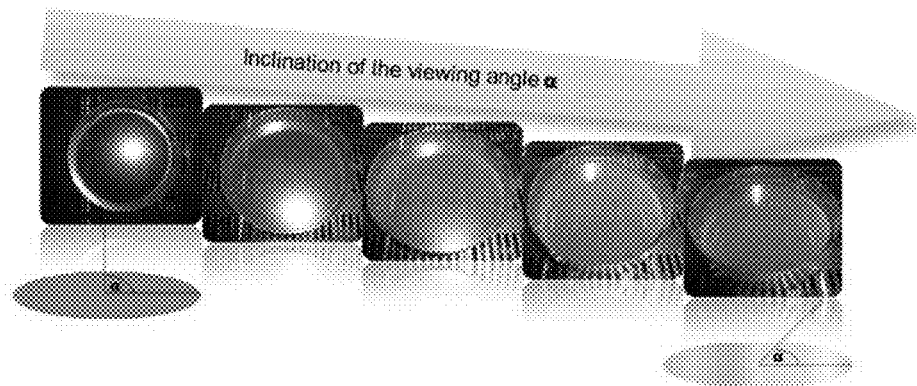
FIG. 11 is an image of a dry film of hybrid microgels of the invention containing $\gamma$-Fe$_2$O$_3$ nanoparticles taken at various viewing angles.

During the drying of a colloidal dispersion of microgels, a film that is transparent and colored in the dry state is obtained which has iridescent properties in reflection at very small viewing angles. The material is then brown (color due to the magnetic nanoparticles) when viewed at 90° and iridescent when viewed at smaller angles (FIG. 11).

Figure 12:
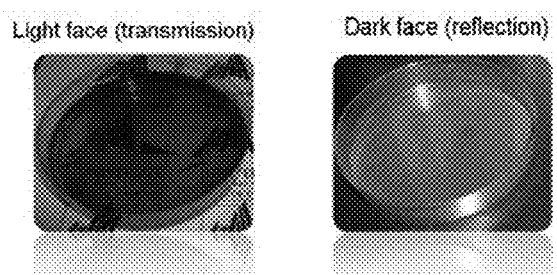
FIG. 12 is an image of a dry film of hybrid microgels of the invention containing $\gamma$-Fe$_2$O$_3$ nanoparticles taken on a light surface and on a dark surface.

The photonic properties are visible in particular in reflection (on dark background) and very little in transmission (on light background) as seen in FIG. 12.

Mechanical and Magnetic Properties of the Hybrid Films

Figure 13:
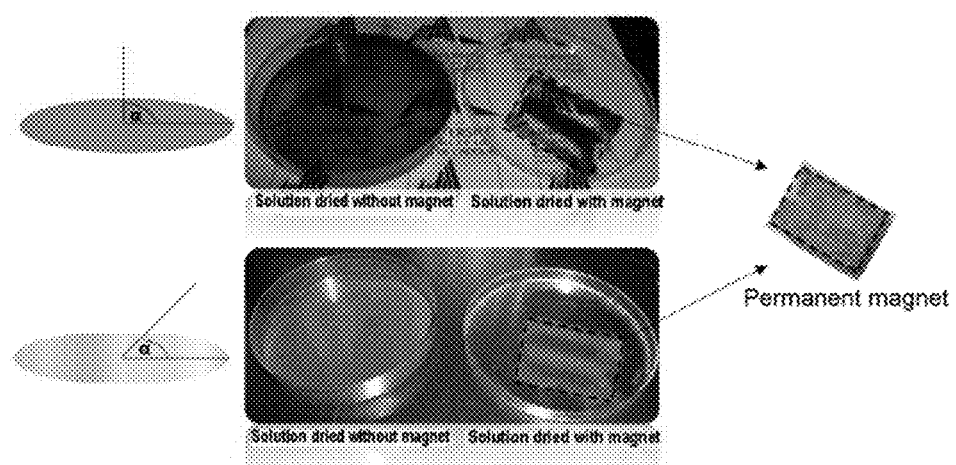
FIG. 13 is an image of a dry film of hybrid microgels of the invention containing $\gamma$-Fe$_2$O$_3$ nanoparticles with and without magnet.

Besides the film formation properties of the hybrid microgels and their optical properties, the addition of magnetic nanoparticles also makes it possible to orient the microgels during the drying. FIG. 13 clearly illustrates these properties since it is possible to concentrate the microgels during the drying at a precise point by application of a magnetic field (in our case the magnet was placed underneath the dispersion). The drying makes it possible, on the one hand, to set everything at a targeted point and, on the other hand, to modify the tint of the final film via a localized concentration of the hybrid microgels while retaining the iridescent properties in reflection (Solution dried with magnet, FIG. 13).

The invention claimed is:

1. Microgels obtained via precipitation polymerization of at least three monomers in an aqueous phase, in the presence of a crosslinking agent, said monomers being:
   di(ethylene glycol) methyl ether methacrylate $M(EO)_2MA$,
   an oligo(ethylene glycol) methyl ether methacrylate having the formula $(M(EO)_nMA)$ wherein n ranges from 3 to 12, and
   methacrylic acid.

2. The microgels as claimed in claim 1, characterized in that the crosslinking agent is selected from the group consisting of oligo(ethylene glycol) diacrylate comprising from 1 to 10 ethylene glycol units, 1,3-butanediol diacrylate, 1,4-butanediol diacrylate, 1,6-hexanediol diacrylate, pentaerythritol diacrylate monostearate, glycerol 1,3-diglycerolate diacrylate, neopentyl glycol diacrylate, poly(propylene glycol) diacrylate, 1,6-hexanediol ethoxylate diacrylate, trimethylolpropane benzoate diacrylate, N,N-divinylbenzene, N,N-methylenebisacrylamide, N,N-(1,2-dihydroxyethylene)bisacrylamide, poly(ethylene glycol) diacrylamide, allyl disulfide, bis(2-methacryloyl)oxyethyl disulfide and N,N-bis(acryloyl)cystamine.

3. The microgels according to claim 1, wherein the oligo(ethylene glycol) methyl ether methacrylate has a Mn being 475 g.mol-1.

4. The microgels according to claim 1, wherein the crosslinking agent is a oligo(ethylene glycol) diacrylate (OEGDA) comprising from 4 to 5 ethylene glycol units.

5. The microgels according to claim 1, wherein the crosslinking agent represents from 1 to 5 mol % of the total number of moles of the three monomers.

6. The microgels according to claim 1, wherein the molar ratio between $M(EO)_2MA$ and $M(EO)_nMA$ is between 1:1 and 20:1.

7. The microgels according to claim 1, wherein $M(EO)_2MA$ represents 80 to 90 mol % of the total number of moles of the three monomers, $M(EO)_nMA$ represents 5 to 15 mol % of the total number of moles of the monomers and methacrylic acid represents 0.1 to 10 mol % of the total number of moles of the monomers, the sum of these three contents being equal to 100%.

8. The microgels according to claim 1, wherein the mean size of the microgels in a dry state may range from 100 to 1000 nm.

9. The microgels according to claim 1, wherein the hydrodynamic radial distribution function of the microgels measured at an angle of 60° and at a temperature of 20° C., is less than 1.1.

10. A cosmetic or pharmaceutical composition comprising the microgels as claimed in claim 1, and at least one compound selected from the group consisting of surfactants, oils, biologically active products, pigments and dyes.

11. The microgels according to claim 6, wherein the molar ratio between $M(EO)_2MA$ and $M(EO)_nMA$ is between 5:1 and 10:1.

* * * * *